United States Patent
Chen et al.

(10) Patent No.: US 10,584,578 B2
(45) Date of Patent: Mar. 10, 2020

(54) SYSTEMS AND METHODS FOR ESTIMATING AND CONTROLLING A PRODUCTION OF FLUID FROM A RESERVOIR

(71) Applicants: Kangping Chen, Scottsdale, AZ (US); Di Shen, Tempe, AZ (US)

(72) Inventors: Kangping Chen, Scottsdale, AZ (US); Di Shen, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 128 days.

(21) Appl. No.: 15/975,186

(22) Filed: May 9, 2018

(65) Prior Publication Data

US 2018/0328168 A1 Nov. 15, 2018

Related U.S. Application Data

(60) Provisional application No. 62/504,182, filed on May 10, 2017.

(51) Int. Cl.
| | |
|---|---|
| *E21B 47/10* | (2012.01) |
| *G01N 11/00* | (2006.01) |
| *E21B 49/08* | (2006.01) |
| *E21B 43/00* | (2006.01) |

(52) U.S. Cl.
CPC .............. *E21B 47/10* (2013.01); *E21B 43/00* (2013.01); *E21B 49/087* (2013.01); *G01N 11/00* (2013.01); *E21B 2049/085* (2013.01)

(58) Field of Classification Search
CPC ........ E21B 47/10; E21B 43/00; E21B 49/087; E21B 2049/085; G01N 11/00
See application file for complete search history.

(56) References Cited

U.S. PATENT DOCUMENTS

| | | |
|---|---|---|
| 7,369,979 B1 | 5/2008 | Spivey |
| 9,790,770 B2 | 10/2017 | King |
| 10,151,515 B2 | 12/2018 | Chen et al. |
| 2002/0096324 A1 | 7/2002 | Poe, Jr. |
| 2003/0050758 A1 | 3/2003 | Soliman |

(Continued)

FOREIGN PATENT DOCUMENTS

WO WO2015077217 A1 5/2015

OTHER PUBLICATIONS

Notice of Allowance in the U.S. Appl. No. 15/378,286 dated Mar. 12, 2019.

(Continued)

*Primary Examiner* — Brad Harcourt
(74) *Attorney, Agent, or Firm* — Snell & Wilmer L.L.P.

(57) ABSTRACT

Disclosed are methods and systems for modeling and controlling production of an oil and/or gas, for example from a shale reservoir. The modeling includes receiving data associated with a fluid reservoir, including a viscosity of a fluid in the reservoir and a radius of a pore in the reservoir, and not including a permeability of the reservoir. The resulting model includes a reservoir fluid drainage rate that is proportional to the fluid viscosity and a reservoir fluid drainage speed that is independent of the pore radius. The model may be used to control a pump which pumps a fluid into and/or out of the reservoir.

14 Claims, 5 Drawing Sheets

(56) References Cited

U.S. PATENT DOCUMENTS

| | | | |
|---|---|---|---|
| 2003/0216898 | A1 | 11/2003 | Basquet |
| 2003/0225522 | A1 | 12/2003 | Poe |
| 2006/0276348 | A1 | 12/2006 | Cowan |
| 2009/0198477 | A1 | 8/2009 | Benish |
| 2009/0294122 | A1 | 12/2009 | Hansen |
| 2010/0137169 | A1 | 6/2010 | Pope |
| 2010/0138196 | A1 | 6/2010 | Hui |
| 2010/0191516 | A1 | 7/2010 | Benish |
| 2010/0286917 | A1 | 11/2010 | Hazlett |
| 2012/0101787 | A1 | 4/2012 | Zhou |
| 2012/0303342 | A1 | 11/2012 | Hazlett |
| 2013/0116998 | A1 | 5/2013 | Shirzadi |
| 2014/0083687 | A1 | 3/2014 | Poe |
| 2014/0136112 | A1 | 5/2014 | Al-Shawaf |
| 2014/0341755 | A1 | 11/2014 | Laing |
| 2015/0120255 | A1 | 4/2015 | King |
| 2015/0211339 | A1 | 7/2015 | Khan |
| 2017/0175513 | A1 | 6/2017 | Chen |
| 2017/0254736 | A1* | 9/2017 | Xu .......................... E21B 43/00 |
| 2018/0202264 | A1 | 7/2018 | Sarduy |

OTHER PUBLICATIONS

Amini et al., Evaluation of the Elliptical Flow Period for Hydraulically-Fractured Wells in Tight Gas Sands—Theoretical Aspects and Practical Considerations, 2007.

FMB, Flowing Material Balance (FMB) Analysis Theory, Dec. 11, 2015.

Final Office Action in the U.S. Appl. No. 15/378,286 dated Jan. 4, 2019.

Non-Final Office Action in the U.S. Appl. No. 15/378,286 dated Jun. 29, 2018.

D.G. Hill, C. Nelson. Gas productive fractured shales: an overview and update. Gas Tips 6, 4-13 (2000).

P.H. Nelson, Pore-throat sizes in sandstones, tight sandstones, and shales. AAPG Bulletin 93, 329-340 (2009).

D. Hughes, Drill, Baby, Drill: Can Unconventional Fuels Usher in a New Era of Energy Abundance? (Post Carbon Institute, Santa Rosa, California, 2013).

X. D. Li, Z. M. Hu, Z. L. Jiang, Continuum perspective of bulk viscosity in compressible fluids. J. Fluid Mech. 812, 966-990 (2017).

F. Javadpour, Nanopores and apparent permeability of gas flow in mudrocks (shales and siltstone). J. Can. Pet. Technol., 48, 16-21 (2009).

C. Clarkson, Production data analysis of unconventional gas wells: Review of theory and best practices. Intl. J. Coal Geol. 109, 101-146 (2013).

S. Rassenfoss, Unconventional rock defies old rules, but new rules are far from being ready. SPE, Sept., 64-66 (2015).

C. L. Cipolla, E. P. Lolon, J. C. Erdle, B. Rubin, Reservoir modeling in shale-Gas reservoirs. SPE Reservoir Eval. & Eng., 13(4), 638-653 (2010).

L. Wang, A. Torres, L. Xiang. X. Fei, A. Naido, W. Wu, A technical review on shale gas production and unconventional reservoirs modeling. Nat. Resour., 6, 141-151 (2015).

M.S. Cramer, Numerical estimates for the bulk viscosity of ideal gases. Phys. Fluids, 24, 066102 (2012).

T. Ertekin, G. A. King, F.C. Schwerer, Dynamic gas slippage: a unique dual-mechanism approach to the flow of gas in tight formations. SPE Form. Eval., 1, 43-52 (1986).

A. Beskok, G.E. Karniadakis, Report: a model for flows in channels, pipes, and ducts at micro and nano scales. Microscale Thermophys. Eng., 3, 43-77 (1999).

F. Javadpour, D. Fisher, M. Unsworth, Nanoscale gas flow in shale gas sediments J. Can. Pet. Technol., 45, 55-61 (2007).

F. Civan, Effective correlation of apparent gas permeability in tight porous media. Transp. Porous Media, 82, 375-384 (2010).

F. Civan, C.S. Rai, C. H. Sondergeld, Shale-gas permeability and diffusivity inferred by improved formulation of relevant retention and transport mechanisms. Transp. Porous Media, 86, 925-944 (2011).

H. Darabi, A. Ettehad, F. Javadpour, K Sepehmoori, Gas flow in ultra-tight shale strata. J. Fluis Mech., 710, 641-658 (2012).

A. Mehmani, M. Prodanovic, F. Javadpour, Multiscale multiphysics network modeling of shale matrx gas flows. Transp. Porous Media, 99, 377-390 (2013).

I Lunati, S. H. Lee, a dual-tube model for gas dynamics in fractured nanoporous shale formations. J. Fluis Mech., 757, 943-971 (2014).

H.-S. Tsein, Siperaerodynamics, mechanics of rarefield gases. J. Aeronautical Sciences, 13, 653-664 (1946).

K.R. Rajagopal, A new development and interpretation of the Navier-Strokes fluid which reveals why the "Stokes assumption" us inapt. Intl. J. Non-Linear Mech. 50, 141-151 (2013).

A. Islam, T. Patzek, Slip in natural gas flow through nanoporous shale reservoirs. J. Uncon. Oil and Gas Resour., 7, 49-54 (2014).

K. Nasrifar, O. Bolland, Prediction of thermodynamic properties of natural gas mixtures using 10 equations of state including a new cubic two-constant equation of state. J. Pet. Sci. Eng., 51, 253-266 (2006).

C. Bousige, C.M. Ghimbeu, C. Vix-Gurterl , A. E. Pomerantz, A. Suleimenova, G. Vaughan, G. Garbarino, M. Feygenson, C. Wildgruber, F. Ulml, R. J..-M. Pellenq, B. Coasne, Realistic molecular model of kerogen's nanostructure. Nature Materials 15, 576-582 (2016).

M. H. J. Hagen, I. Pagonabarraga, C.P. Lowe, D. Frenkel, Algerbaic decay of velocity fluctuations in a confined fluid. Phys. Rev. Ltr, 78 (19), 3785-3788 (1997).

B.U. Felderhof, Transient flow of a viscous compressible fluid in a circular tube after a sudden point impulse. J. Fluid Mech., 644, 97-106 (2010).

R.E. Graves and B.A. Argrow, Bulk viscosity: past to present. J. Thermophys. Heat Transfer, 13, 337-342 (1999).

\* cited by examiner

SYSTEMS AND METHODS FOR ESTIMATING AND CONTROLLING A PRODUCTION OF FLUID FROM A RESERVOIR

CROSS-REFERENCE TO RELATED APPLICATIONS

This application claims priority to, and the benefit of, U.S. Provisional Patent No. 62/504,182 filed on May 10, 2017, and entitled "SYSTEM AND METHOD FOR ESTIMATING AND CONTROLLING PRODUCTION OF FLUID FROM A RESERVOIR," the entire contents of which are incorporated by reference herein for all purposes.

TECHNICAL FIELD

This disclosure relates to oil and gas production, and more particularly relates to systems and methods for estimating and controlling a production of oil and gas from a shale reservoir.

BACKGROUND

Despite the impact of the "shale revolution" on global energy supply, why oil and gas can be produced in large quantities from the nano-pores of shale within a one-year time span still defies scientific explanation. Porous media flow theory based on Darcy's law predicts that it should take natural gas more than 70 years to migrate just one meter in the ultra-tight shale matrix having permeability as low as one nano-darcy (which is six orders of magnitude lower than the mini-darcy range for conventional reservoirs). The magnitude of shale oil production is even more unanticipated due to the high shear viscosity of oil. To date, scientists have not yet reconciled the current booming shale oil and gas production with the oil and gas production estimates provided by conventional models that are based on Darcy's law. That is, conventional oil and gas production models based on Darcy's law are incapable of estimating oil and gas production from a shale reservoir. Accordingly, improved assessment and/or evaluation techniques and related systems remain highly desirable.

SUMMARY

Embodiments of this disclosure may include methods and systems for estimating and/or controlling a production of oil and gas from a shale reservoir. In particular, a method for estimating a production of fluid from a reservoir may include: receiving, by a processor, a data associated with a fluid reservoir, wherein the data comprises at least a fluid viscosity in the reservoir and a pore radius in the reservoir, and wherein the data does not include a permeability of the reservoir, and modeling, by the processor and based, at least in part, on the data, a fluid production model comprising a reservoir fluid drainage rate that is proportional to the fluid viscosity, a reservoir fluid drainage speed that is independent of the pore radius and permeability, and a fluid drain-out time comprising a time when a total amount of fluid mass produced from the reservoir has reached a percentage of a producible fluid mass value.

In another embodiment, a non-transitory computer-readable medium may have program code recorded thereon. The program code may include: program code for causing a computer to receive data associated with a fluid reservoir, wherein the data comprises at least a fluid viscosity in the fluid reservoir and a pore radius in the fluid reservoir, and wherein the data does not include a permeability of the fluid reservoir; and program code for causing the computer to model a production of fluid from the fluid reservoir based, at least in part, on the data, wherein the model includes a reservoir fluid drainage rate that is proportional to the fluid viscosity, a reservoir fluid drainage speed that is independent of the pore radius and permeability, and a fluid drain-out time that provides a time when the total amount of fluid mass produced from the reservoir has reached a percentage of producible fluid mass value.

In yet another embodiment, an apparatus configured for estimating a production of fluid from a reservoir may include at least one processor; and a memory coupled to the at least one processor. The at least one processor may be configured to: receive data associated with a fluid reservoir, wherein the data comprises at least a viscosity of a fluid in the reservoir and a radius of a pore in the reservoir, and wherein the data does not include a permeability of the reservoir; and model a production of fluid from the reservoir based, at least in part, on the received data, wherein the model includes a reservoir fluid drainage rate that is proportional to the fluid viscosity and a reservoir fluid drainage speed that is independent of the pore radius and permeability.

According to another embodiment, an apparatus for producing fluid from a reservoir may include: a pump which pumps a first fluid into a fluid reservoir that includes a second fluid; and a controller which controls the pump in accordance with a reservoir fluid production model, wherein the reservoir fluid production model comprises at least a reservoir fluid drainage rate that is proportional to a viscosity of the second fluid in the reservoir and a reservoir fluid drainage speed that is independent of a radius of a pore in the reservoir.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments.

DETAILED DESCRIPTION

Figure 1:
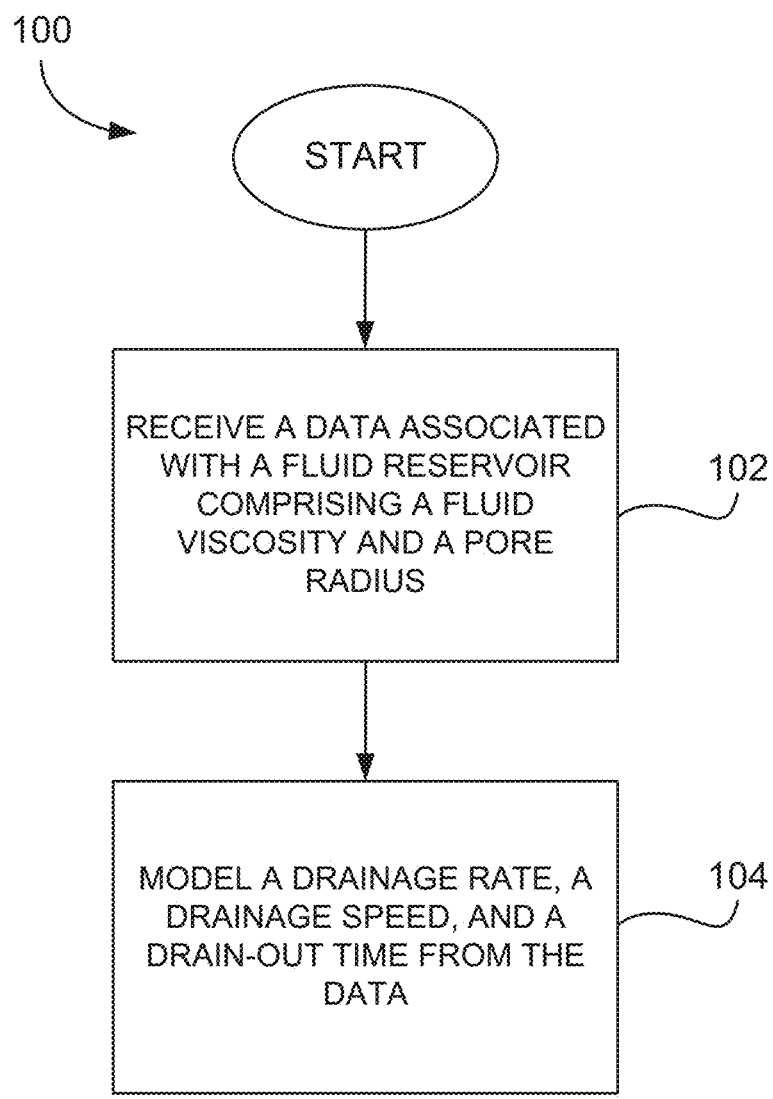
FIG. 1 illustrates a flow chart of an exemplary method for estimating fluid production from a reservoir in accordance with the present disclosure.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for petroleum and/or natural gas production, hydraulic fracturing, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical system or method for estimating and/or controlling production of a fluid from a reservoir.

Embodiments of this disclosure may provide methods and systems for estimating and controlling the production of oil and gas fluid from a shale reservoir based on models that do not follow Darcy's law. That is, exemplary models and approaches utilized in accordance with this disclosure illustrate that primary petroleum production, which is driven by the volumetric expansion of the in situ petroleum fluids, does not follow Darcy's law. For example, models developed in accordance with this disclosure include a model of drainage rate that is directly proportional to fluid viscosity, which is in contrast to Darcy's law because Darcy's law provides that drainage rate is inversely proportional to fluid viscosity. Additionally, models developed in accordance with this disclosure include a model of drainage speed that is independent of the pore radius, which is in contrast to Darcy's law because Darcy's law provides that a drainage speed is proportional to the square of the pore radius. Therefore, while Darcy's law fails to explain why oil and gas can be extracted from the nano-pores of shale, embodiments of this disclosure can be used to estimate oil and gas production from shale reservoirs. Stated another way, principles of the present disclosure illustrate unexpected results and deviate significantly from conventional understanding in the relevant field.

Even after hydraulic fracturing, fluid still has to travel from the ultra-tight nano-pores of a shale matrix block to the surrounding fractures before it can then move to a wellbore. When the shale matrix permeability is 100 nano-darcy, porous media flow theory based on Darcy's law predicts that, under typical shale conditions, gas moves at a speed less than 1 nanometer per second in the shale matrix even for a high pressure gradient of 2 kPa per meter, and therefore, it would take more than 70 years for it to migrate just one meter. Shale oil production is even more unimaginable due to oil's high shear viscosity. Reconciling such a dire prediction with the reality of on-going booming shale production has been a huge challenge for the scientific community.

Previous studies have focused on gas transport through nano-scale capillaries, and are essentially modifications to Poiseuille's law and Darcy's law. Poiseuille's law for compressible flow in a capillary gives a volumetric flow rate with the radius and length of the capillary, respectively, and the inlet and outlet pressures. The macroscopic Darcy's law can be obtained from the pore-scale capillary tube model by setting the permeability, the porosity and the tortuosity of the medium respectively. Most popular among the recent works is the slip theory which postulates that gas slips in nano-size capillaries, and such slippage enhances flow rate. This slip theory, however, is based on rarefied gas dynamics and the kinetic theory for dilute gas, and it is generally not applicable to shale gas as natural gas is a supercritical fluid with high density under the pressure in typical shale reservoir conditions (and above). Slip may occur for gas in extremely small capillaries (e.g., less than 10 nanometers in diameter) when the pressure is below 10 MPa. These extremely small pores, however, are associated with organic matter that stores gas in an adsorbed phase, and they hold very little free gas compared to the dominant larger inorganic pores in the shale matrix. Desorption is a much slower process and there is no evidence suggesting that the initially immobile adsorbed gas has been produced in the first year. Furthermore, a recent study shows that these extremely small organic nano-pores actually trap oil and gas molecules instead of allowing them to flow. Thus, the slip theory is highly questionable for shale gas production. No theory has been proposed to explain why oil can also be produced efficiently from the ultra-tight shale matrix. To date, fluid production from shale has defied explanation using fluid dynamics theory.

In contrast, principles of the present disclosure illustrate that the drainage speed is proportional to the kinematic viscosity of the fluid and the drainage speed is independent of the pore diameter. When this result is up-scaled to a macroscopic level, the production rate becomes dependent on porosity but independent of permeability. This result is in stark contrast to the prior approaches, which give a production rate proportional to permeability. Permeability is a property of the rock and the fluid and it is very difficult to measure and simulate. This gives the present approach an advantage over the prior approaches.

With initial reference to FIG. 1, a flow chart illustrating a method 100 for estimating a production of fluid from a reservoir in accordance with the present disclosure is illustrated. At block 102, method 100 comprises receiving, by a processor, data associated with a fluid reservoir, wherein the data includes at least a viscosity of a fluid in the reservoir and a radius of a pore in the reservoir, and wherein the data does not include a permeability of the reservoir. In various embodiments, the fluid reservoir may include a shale reservoir, and the fluid may include oil and/or gas.

At block 104, method 100 comprises modeling, by the processor, a production of fluid from the reservoir based, at least in part, on the received data, wherein the model utilizes a reservoir fluid drainage rate that is proportional to the fluid viscosity and a reservoir fluid drainage speed that is independent of the pore radius. In various embodiments, the production of fluid from the reservoir may also be modeled with a fluid drain-out time that provides a time when the total amount of fluid mass produced from the reservoir has reached a percentage of producible fluid mass value.

In various exemplary embodiments, the model developed at block 104 may be based on Navier-Stokes equations with no-slip condition and without additional hypothesis. Fluid production from a shale matrix to surrounding fractures may be modeled by a damped acoustic wave in a "huff-n-puff" pumping process.

Figure 3:
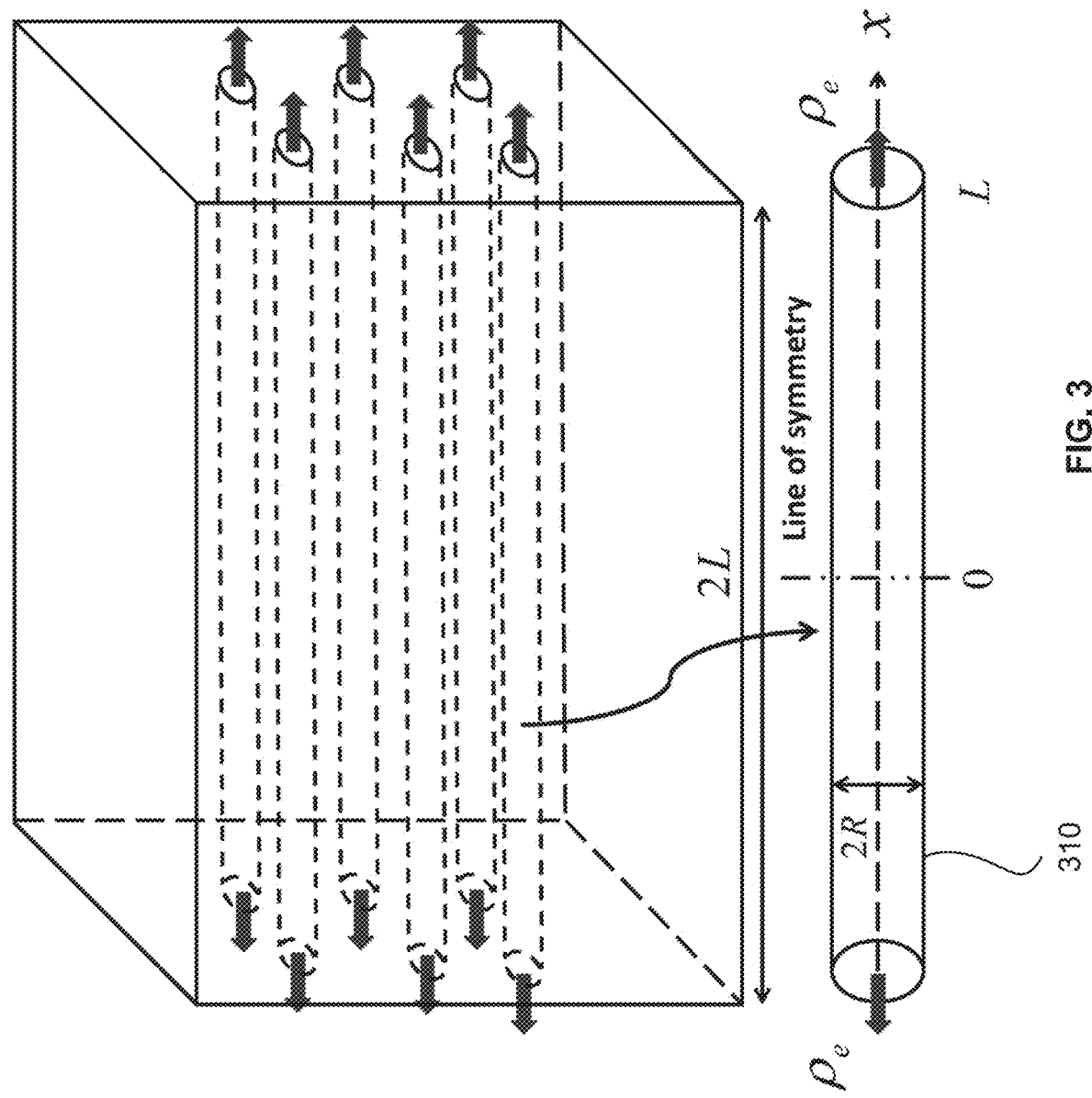
FIG. 3 illustrates a model for calculating drainage from a capillary tube embedded in a shale matrix block surrounded by fractures in accordance with the present disclosure.

With reference now to FIG. 3, production of a fluid (for example, a natural gas or a liquid petroleum product) from shale can be modeled as pore-scale volume-expansion-driven drainage flow of a single phase compressible fluid from a small capillary tube 310 embedded in a matrix block with its ends open to surrounding fractures. The tube 310 has an inner radius R and length 2L. The fluid stored in tube 310 can be gas or liquid and it is initially at rest with a density $\rho_i$. The fluid is drained symmetrically from both ends of the tube 310 upon lowering the density at the ends to $\rho_e$. Fluid in the fractures is maintained at the density $\rho_e$. In practice, in order to maintain mechanical integrity of the block and the adjacent fractures, the exit density (or pressure) is lowered gradually by multiple small steps during production. In each step, the density perturbation can be considered as small and temperature variation is negligible. The Mach number is small so that nonlinear inertial effect can be neglected. The continuity and the compressible Navier-Stokes equations linearized around the new equilibrium state become:

$$\frac{\partial \rho'}{\partial t} + \rho_e \nabla \cdot v' = 0, \text{ and}$$

$$\rho_e \frac{\partial v'}{\partial t} = -\nabla p' + \left(\mu_b + \frac{1}{3}\mu\right)\nabla(\nabla \cdot v') + \mu \nabla^2 v',$$

where the density perturbation $\rho' = \rho - \rho_e$; p' is the pressure perturbation; v' is the velocity perturbation which is assumed to be axisymmetric; and $\mu$, $\mu_b$ are the shear and bulk viscosities of the fluid, respectively. From the Helmholtz decomposition theorem, the velocity field v' can be decomposed into the sum of an irrotational part $v'_{IR}$ and a rotational part $v'_{RT}$, $v' = v'_{IR} + v'_{RT}$, with the rotational part being solenoidal (incompressible), $\nabla \cdot v'_{RT} = 0$. These two parts of the velocity field are called the longitudinal mode and transverse mode respectively in the acoustic literature. The total velocity v' satisfies the no-slip condition on the tube wall, r=R: $v' = v'_{IR} + v'_{RT} = 0$.

The density perturbation is governed by a damped wave equation:

$$\frac{\partial^2 \rho'}{\partial t^2} = \left(c^2 + D_\rho \frac{\partial}{\partial t}\right)\nabla^2 \rho',$$

where the diffusion coefficient $D_\rho = (\mu_b + 4\mu/3)/\rho_e$ characterizes the diffusion of a small density disturbance and c is the speed of sound ($p' = c^2\rho'$). Because of symmetry about x=0, only one-half of the tube needs to be considered. The density perturbation equation can be solved analytically subject to the boundary and initial conditions x=0:$\partial\rho'/\partial x = 0$; x=L: $\rho'=0$; t=0: $\rho'=\rho_i-\rho_e$, $\partial\rho'/\partial t=0$. For typical shale gas and oil properties and tubes of micron-size or smaller, after a very short time (e.g., $\approx 10^{-7}$ s), the density quickly relaxes to a profile uniform over the tube cross-section (i.e. the plane wave solution) with the density perturbation given by $$\rho'(x, t) = \frac{4(\rho_i - \rho_e)}{\pi} \sum_{n=0}^{N_d} \frac{(-1)^n}{2n+1} \exp(-\gamma_n t)\cos\omega_n t \cos\frac{(2n+1)\pi x}{2L},$$

where $\gamma_n = (2n+1)^2 \pi^2 D_\rho/8L^2$, $\omega_n = (2n+1)\pi c[1-(2n+1)^2 \pi^2 D/16c^2 L^2]^{1/2}/2L$.

Here, $N_d$ is a large integer such that q becomes imaginary when $n > N_d$. For L=1 m and typical shale gas and oil property values, $N_d \approx 10^7$. For simplicity, the purely diffusive modes from $n > N_d$ in the infinite series have been neglected since they decay at a much faster rate. The density solution represents a damped standing acoustic wave with a density node at the tube exit x=L and an antinode at x=0. With reference again to FIG. 3, instantaneous density and instantaneous velocity field for the first half cycle (rarefaction wave, production phase) of density oscillation of gas (methane) are illustrated. L=1 meter, R=10 micrometers, and period T=0.0068 seconds. The cycle starts at t=68 seconds. Time instants in the cycle are: A: T/8, B: T/4, and C: 3T/8. Arrows indicate the directions of wave propagation. Shading in the velocity plots indicates velocity magnitude. The second half-cycle compression wave (suction phase) is essentially the reverse of the first-half cycle, except the amplitude is reduced (not shown). In this illustration, a radius of 10 micrometers is chosen in order to see details but the pattern remains the same for nano-pores.

Physically, when the density at the tube exit is dropped from $\rho_i$ to $\rho_e$, a rarefaction wave is initiated from the exit (x=L), which propagates inward in the capillary towards the symmetry line (x=0). The rarefaction wave then reflects from the symmetry line and propagates towards the exit. Since the density at the exit is fixed, this wave cannot escape from the tube. The trapped wave then turns around and propagates inward towards the symmetry line as a compressive wave. The amplitude of the wave always decays in time due to the inward longitudinal diffusion of the density perturbation from the tube exit.

For the relaxed density profile, the irrotational velocity is longitudinal and independent of the radial coordinate r, $v'_{IR} = v'_{x,IR}(x,t)e_x$, and it can be determined from the continuity equation, $$v'_{x,IR}(x, t) =$$

$$\frac{8L}{\pi^2}\frac{\rho_i - \rho_e}{\rho_e}\sum_{n=0}^{N_d}\frac{(-1)^n}{(2n+1)^2}\exp(-\gamma_n t)(\gamma_n\cos\omega_n t + \omega_n\sin\omega_n t)\sin\frac{(2n+1)\pi x}{2L}.$$

The solenoidal velocity $v'_{RT}$ is two-dimensional and it is determined by the incompressibility condition and the vorticity diffusion equation with the wall condition r=R: $v'_{RT}=-v'_{IR}$. The stream-function solution for $v'_{RT}$ is given by the real part of:

$$\psi = \frac{8L}{\pi^2}\frac{\rho_i - \rho_e}{\rho_e}r$$

$$\sum_{n=0}^{N_d}\frac{(-1)^n}{(2n+1)^2}\frac{\Omega_n e^{\Omega_n t}}{F_n(R)}\frac{J_1(\alpha_n R)J_1(\sigma_n r) - J_1(\sigma_n R)J_1(\alpha_n r)}{J_1(\alpha_n R)}\sin\frac{(2n+1)\pi x}{2L},$$

where $J_n$ is the nth-order Bessel function of the first kind, and:

$$F_n(r) = \frac{\sigma_n J_1(\alpha_n R)[J_0(\sigma_n r) - J_2(\sigma_n r)] - \alpha_n J_1(\sigma_n R)[J_0(\alpha_n r) - J_2(\alpha_n r)]}{2J_1(\alpha_n R)},$$

$$\Omega_n = -\gamma_n + i\omega_n; \; \alpha_n = i\left[\frac{(2n+1)^2\pi^2}{4L^2} + \frac{\Omega_n}{\nu_e}\right]^{1/2}; \; \sigma_n = i\frac{(2n+1)\pi}{2L}; \; \nu_e = \frac{\mu}{\rho_e}.$$

The solenoidal velocity, however, gives a zero mass flow rate over any cross-section of the tube, since $\nabla \cdot v'_{RT}=0$ implies that the volumetric flow rate Q(x)=constant=Q(0)=0 for symmetric draining. Thus, the role of the solenoidal velocity is to enforce the no-slip condition on the tube wall for the overall velocity and it has no effect on the drainage rate.

For large tubes, the stream-wise solenoidal velocity $v'_{x,RT}$ is the classical Stokes solution driven by an oscillatory boundary. As the tube radius is reduced, the Stokes layer thickness becomes larger and it exceeds the tube radius for very small tubes. $v'_{x,RT}$ has the asymptotic expression in the small radius limit:

$$v'_{x,RT} = v'_{x,IR}\left[\left(1 - 2\frac{r^2}{R^2}\right) + O\left(\frac{cR^2}{v_e L}\right)\right].$$

For L=1 meter and typical property values of shale oil and gas, $v'_{x,RT}$ can be very well approximated by the above parabolic profile for a tube radius below 1 micrometer. The overall stream-wise velocity in the small radius limit is then:

$$v'_x = \frac{16L}{\pi^2} \frac{\rho_i - \rho_e}{\rho_e}\left(1 - \frac{r^2}{R^2}\right)$$
$$\sum_{n=0}^{N_d} \frac{(-1)^n}{(2n+1)^2} \exp(-\gamma_n t)(\gamma_n \cos\omega_n t + \omega_n \sin\omega_n t) \sin\frac{(2n+1)\pi x}{2L},$$

which is parabolic and satisfies the no-slip condition on the wall. This parabolic velocity profile, however, differs significantly from that of a Poiseuille flow: the centerline velocity is independent of the tube radius; whilst the centerline velocity of a Poiseuille flow is proportional to $R^2$. Furthermore, the velocity is not inversely proportional to shear viscosity as in Poiseuille flow. The new analytical solution can be confirmed using commercially-available physics modeling software.

The instantaneous mass flow rate at the tube exit is given by:

$$\hat{m}_e(t) = \frac{8R^2L(\rho_i - \rho_e)}{\pi} \sum_{n=0}^{N_d} \frac{\exp(-\gamma_n t)}{(2n+1)^2}(\gamma_n \cos\omega_n t + \omega_n \sin\omega_n t)$$

Thus, the mass flow rate oscillates in time with a frequency of $\omega_0 = \pi c/2L$, generally in the range over 100 Hz for shale oil and gas when L=1 meter. Thus, in the first half-period of oscillation (rarefaction phase), fluid is produced from the capillary; and in the second half-period (compressive phase), fluid is sucked back into the tube. Since the amplitude of density oscillation always decays in time and the cycle starts from the production phase, there is a net positive mass production after each oscillation period as the fluid mass inside the tube decreases. The drainage rate $\hat{m}_e(t)$ is the period-averaged net mass flow rate which is also the mass decrease in the tube per period divided by the period T (=4L/c):

$$\hat{m}_e(t) = \frac{M(t) - M(t+T)}{T} = \frac{1}{T} \frac{8(\rho_i - \rho_e)R^2L}{\pi} \sum_{n=0}^{N_d} \frac{1 - \exp(-\gamma_n T)}{(2n+1)^2} \exp(-\gamma_n t).$$

When t>>T, the higher modes (large n) experience large exponential decay and their contributions to the drainage rate are negligible. The lower modes can be approximated by keeping just one term in the Taylor series expansion for $1 - \exp(-\gamma_n T)$. Thus, the leading order expression for the drainage rate is:

$$\hat{m}_e(t) = M_L \frac{D_\rho}{L^2} \sum_{n=0}^{N} \exp\left[-\frac{D_\rho(2n+1)^2\pi^2 t}{8L^2}\right],$$

where $M_L = \pi R^2 L(\rho_i - \rho_e)$ is the total amount of producible fluid from half of the capillary (length of L) for a given density drop $\rho_i - \rho_e$; N is the cut-off integer so that $\gamma_n T = (2n+1)^2\pi^2 D_\rho/2cL < 1$ for $n < N(N \approx 10^3$ for shale oil and gas with L=1 meter). Since the period T for a meter-size block is typically of the order of 0.01 second, the drainage rate expression can be used virtually for all times of interest to fluid production. A period-averaged drainage speed corresponding to the drainage rate can be defined as:

$$V_e(t) = \frac{\hat{m}_e(t)}{\rho_e \pi R^2} = \frac{\rho_i - \rho_e}{\rho_e} \frac{D_\rho}{L} \sum_{n=0}^{N} \exp\left[-\frac{D_\rho(2n+1)^2\pi^2 t}{8L^2}\right].$$

Figure 4:
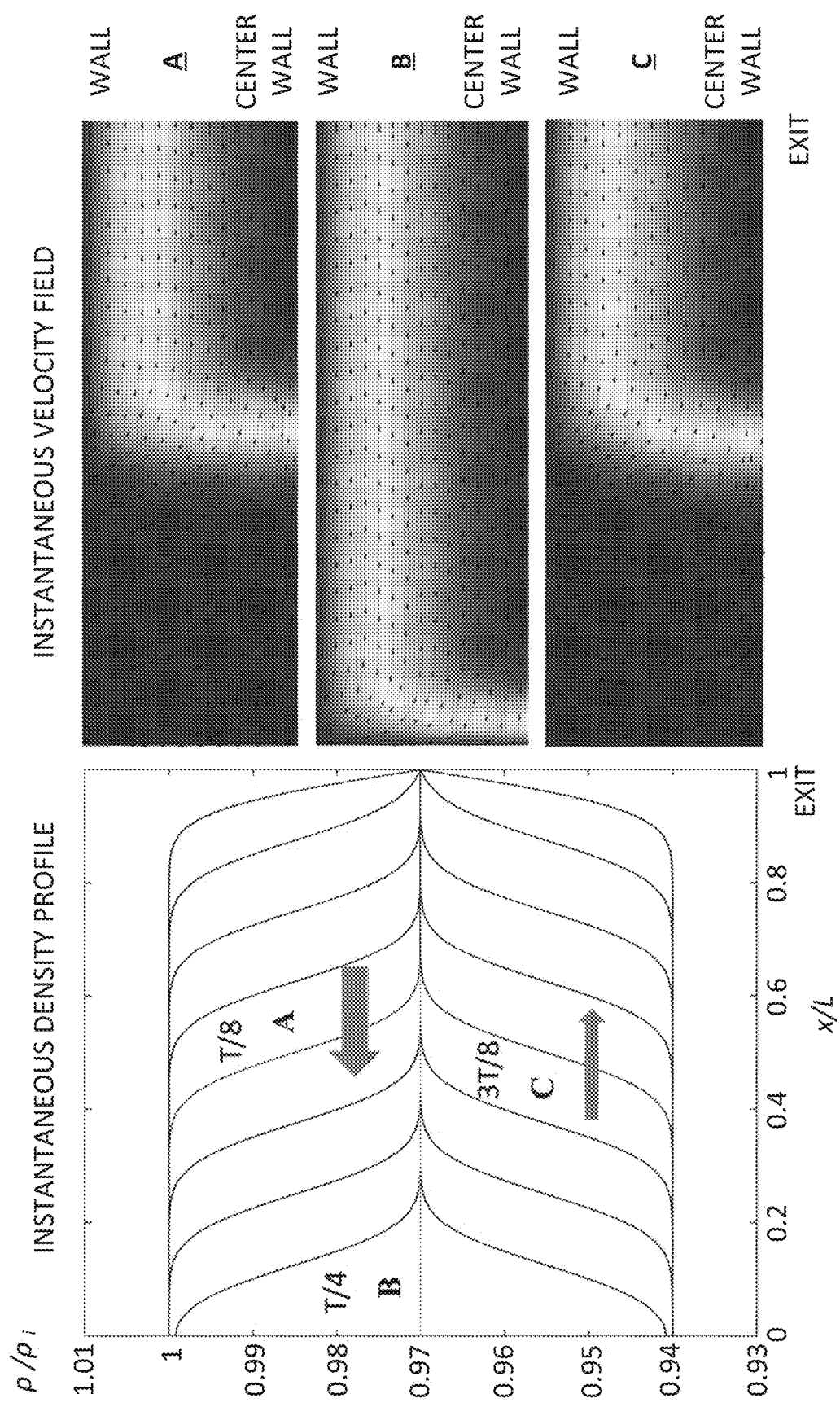
FIG. 4 illustrates a model of a damped acoustic standing wave with a density node at the tube exit and an antinode at x=0 in accordance with the present disclosure.

The result above shows that fluid is produced from the capillary in an oscillatory "huff-n-puff" pumping process driven by the decaying standing acoustic wave trapped inside the capillary. The drainage rate obtained by integrating the instantaneous mass flow rate over a period smooths out the fast oscillation, leaving the longitudinal diffusion of the density perturbation as the only traceable footprint in the drainage rate expression on a time scale much larger than the period of oscillation. This short-time to long-time coupling is embedded in the damped wave equation for the density perturbation. Although the confinement of the fluid to a very narrow tube smooths out the transverse variation of density quickly, damping of the longitudinal variation of density is extremely slow, giving the acoustic wave a long life-time. The drainage $\hat{m}_e(t)$ is determined by the slow diffusive time scale and it is independent of the oscillation frequency. Since the diffusion coefficient $D_\rho = (\rho_b + 4\mu/3)/\rho_e$, the drainage rate is proportional to the combined bulk and shear viscosities $\mu_b + 4\mu/3$ and the square of the tube radius $R^2$. This is a stark contrast to the classical Poiseuille's law which gives a drainage rate inversely proportional to the shear viscosity $\mu$ and proportional to the quartic power of the tube radius $R^4$. Poiseuille's law is only appropriate for displacement flows, and it is not suitable for the current fluid-volume expansion-driven drainage flow. The longitudinal diffusive nature of the drainage flow is also manifested by the appearance of the diffusive velocity scale $D_\rho/L$ in the drainage speed $V_e(t)$. This drainage speed is the average Lagrangian velocity for the fluid particles that have exited the tube during one period of oscillation, and it differs significantly from the instantaneous Eulerian velocity at the tube exit. For example, the drainage speed for gas in a 10 micrometer radius tube for the cycle shown in FIG. 4 (t=68 seconds) is 10.24 micrometers per second, whilst the instantaneous velocity at the centerline of the exit is as high as 36.12 meters per second during the cycle. Thus, while the instantaneous flow field is highly oscillatory with a high speed and high frequency, the drainage speed is very low. Despite the high instantaneous velocity, however, the oscillation in the displacement of a fluid particle remains small during the period, no more than 3 centimeters for the case shown in FIG. 4.

An outstanding feature of the drainage speed is that it is independent of the capillary radius. For the case shown in FIG. 4, if the tube radius is reduced from 10 micrometers to 10 nanometers while maintaining the same density drop $\rho_i - \rho_e$, the drainage speed will still be 10.24 micrometers per second at t=68 seconds. In other words, regardless how small a capillary is, a compressible fluid, gas or liquid, can escape the capillary with a finite speed, even though the mass flow rate might be small due to its $R^2$ dependence on the capillary radius. Poiseuille's law, on the other hand, predicts an average exit speed proportional to $R^2$ and inversely proportional to the shear viscosity, giving rise to an infinitesimally small exit velocity for very small capillaries.

Once the producible fluid mass $M_L$ is given, the diffusion coefficient $D_\rho$ is the only fluid property that the drainage rate $\hat{m}_e(t)$ depends on. $D_\rho$ is directly related to the bulk viscosity $\mu_b$. It is well recognized that Stokes' hypothesis of zero bulk viscosity is only valid for dilute monatomic gas. While data on bulk viscosity of fluids are still scarce, the bulk viscosity for a liquid is generally of the same order of magnitude as its shear viscosity. On the other hand, the bulk viscosity of a polyatomic gas increases with temperature and it can become several orders of magnitude higher than its shear viscosity in a wide temperature range. These high gas bulk viscosity values are supported by measurements of relaxation times. In particular, the bulk viscosity for methane, the dominant component of natural gas, is estimated to be 320 times of its shear viscosity at 80° C., a temperature typical for shale. At 80° C. and a pressure of 25 MPa, the diffusion coefficients for gas and oil are of the same order of magnitude, $D_\rho=4.82\times10^{-5}$ m²/s, and $D_\rho=8.43\times10^{-6}$ m²/s, respectively, and they differ only by a multiple of 5.72. Thus, we conclude that viscous oil can be produced from small capillaries as efficiently as gas, even though their shear viscosities differ by at least two orders of magnitude.

Figure 5:
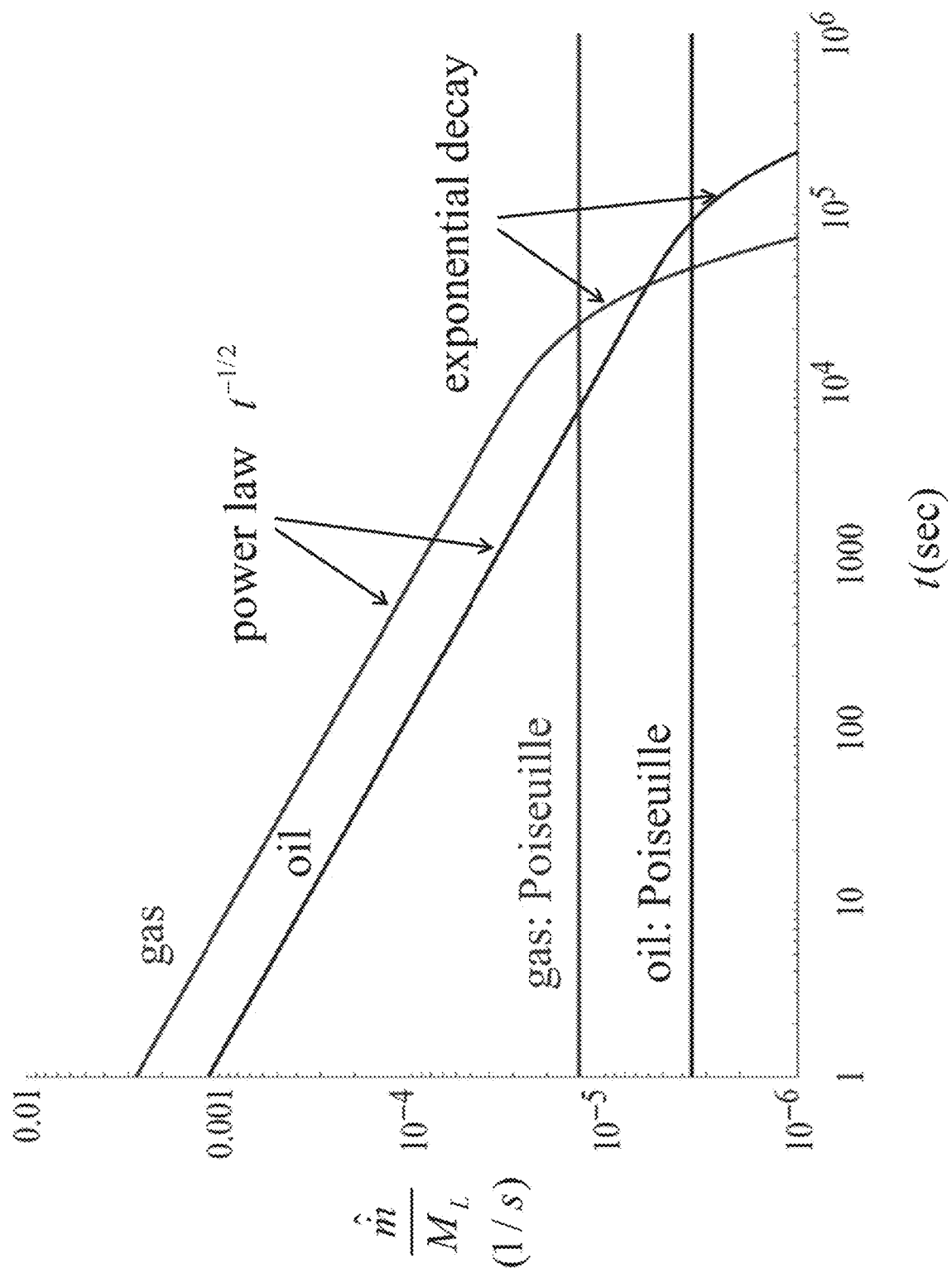
FIG. 5 illustrates a logarithmic plot of a scaled drainage rate of a fluid reservoir over time in accordance with the present disclosure.

With reference now to FIG. 5, a scaled drainage rate versus time is plotted on log-log scale for shale oil and gas. In early times, these drainage rates are two-orders of magnitude higher than those given by the Poiseuille's law (the Posieuille's law result is for radius of 10 nanometers). The straight-line portion of the curves corresponds to a power law for the drainage rate, $\hat{m}_e(t) \approx t^{1/2}$, typical for diffusive transport. The power law ends when the density diffusion front reaches x=0, thereafter the drainage rate decays exponentially to zero. A drain-out time $t_{d,\Delta}$, defined as the instant when the accumulative produced fluid mass has reached 99% of the producible mass, can be used to measure how fast a fixed amount of stored fluid is produced. This drain-out time is:

$$t_{d,\Delta} = 3.57 \frac{L^2}{D_\rho}.$$

A unique feature of the $\hat{m}_e(t)/M_L$ curves in FIG. 5 is that the area underneath each curve is always unity, reflecting the fact that the accumulative fluid production is the producible mass $M_L$. A large diffusion coefficient $D_\rho$ gives a large drainage rate as well as a small drain-out time. Contrary to intuition, a large drainage rate accompanied by a small drain-out time is actually beneficial for fluid production for drainage flows, as a fixed amount of fluid is produced in a shorter time. This characteristic is quite different from open-end tube flows for which maintaining a high drainage rate produces more fluids due to unlimited supply of fresh fluid from upstream. FIG. 5 further illustrates that the drainage rates for oil and gas are of the same order of magnitude. Furthermore, the drain-out time ratio between oil and gas is $t_{d,oil}/t_{d,gas}=D_{\rho,gas}/D_{\rho,oil}=5.72$. Thus, oil and gas can be produced from the capillary in a similar time span. The classical Poiseuille theory, on the other hand, gives a significantly larger drain-out time ratio $t_{d,oil}/t_{d,gas}=\mu_{oil}/\mu_{gas}=145$, as the drain-out time from the Poiseuille theory is proportional to the shear viscosity $\mu$.

In addition to the unified fluid production mechanism at the pore scale elucidated above, macroscopic phenomena observed during shale production can also be explained in terms of the exemplary principles of the present disclosure. Because a matrix block in fractured shale is drained simultaneously from six sides, the drainage rate from a cubic matrix block with sides of 2L and uniform size capillaries is given by:

$$\hat{m}_B(t) = 3 M_B \frac{D_\rho}{L^2} \sum_{n=0}^{N} \exp\left[-\frac{D_\rho(2n+1)^2\pi^2 t}{8L^2}\right],$$

where $M_B=8(\rho_i-\rho_e)\phi L^3$ is the producible fluid inside the block for a given density drop. The small block size created by the massive hydraulic fracturing boosts the drainage rate from each block. There are hundreds of thousands, even millions, of such blocks in the fracture stimulated reservoir volume (SRV) and they feed simultaneously to the fluid flow in the fracture network. This leads to the observed high production rate at the wellbore. The small block size also contributes to the observed fast drop-off in the production rate. As discussed earlier, this fast drop-off in the production rate is indicative of efficient fluid draining. The high production rate is maintained by repeatedly lowering the exit density in small steps. The observed low recovery factor, on the other hand, is due to the inclusion of the adsorbed fluid in the estimated amount of fluid-in-place. The adsorbed phase can only be harvested over a much longer time frame and additional stimuli are likely required to recover this part of the reserves. The estimated maximum 15% recovery factor likely indicates that all recoverable mobile phase petroleum fluid has already been produced, since the adsorbed fluid makes up as much as 85% of the total fluid-in-place.

In various embodiments, the production of a fluid from a reservoir may be estimated, controlled, modified, or otherwise performed based on at least one parameter calculated by the herein described modeling methods. For example, one or more of the drainage rate, drainage speed, or drain-out time can be estimated and used during production of oil or gas from a shale reservoir. For example, in an embodiment, the step of modifying the production of fluid from the reservoir may include modifying a pressure applied to the reservoir based on at least one of the drainage rate, drainage speed, or drain-out time. According to one embodiment, the step of modifying the pressure may include reducing pressure based on at least one of the drainage rate, drainage speed, or drain-out time. In particular, in one embodiment, the step of modifying the pressure may include stopping the production of fluid from the reservoir based on at least one of the drainage rate, drainage speed, or drain-out time.

Figure 2:
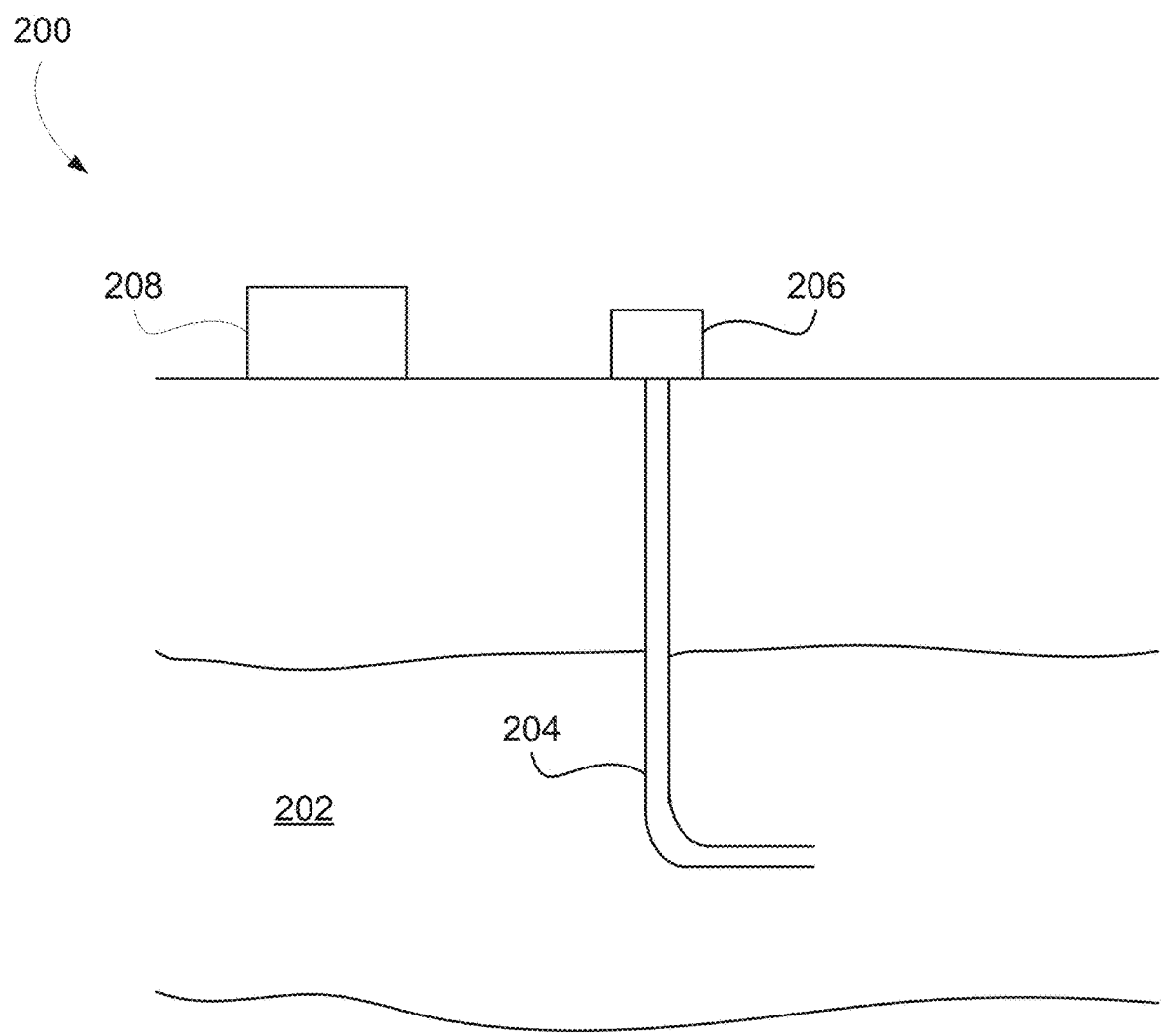
FIG. 2 illustrates a diagram of an exemplary system for producing fluid from a reservoir in accordance with the present disclosure.

With reference now to FIG. 2, a system 200 for controlling the production of a fluid from a reservoir in accordance with the present disclosure is illustrated. In various embodiments, system 200 includes a shale reservoir 202, a well 204 for drawing oil and/or gas from the shale reservoir, a wellhead 206, and a pump 208. The pump 208 may be configured to pump a first fluid into the fluid reservoir. In various embodiments, the first fluid may include a water-based fluid comprising water, sand, and/or chemical additives. In certain embodiments, the pump 208 may include one or more pumps 208, such as a plurality of pumps 208. According to one embodiment, the one or more pumps 208 may be located near the well 204 on a ground surface. In another embodiment, the one or more pumps 208 may be located on a pump truck.

A controller configured to control the pump 208 may be located on, or within, the pump 208 or the wellhead 206. Alternatively, the controller may be remotely coupled to and/or in electronic communication with the pump 208. In various embodiments, the controller may be a computer or a computing device. The controller may be configured to control the pump 208 in accordance with a reservoir fluid production model that includes a model of a reservoir fluid drainage rate that is proportional to a viscosity of the fluid in the reservoir and a model of a reservoir fluid drainage speed that is independent of a radius of a pore in the reservoir. In various embodiments, the model may also include a fluid drain-out time that provides a time when the total amount of fluid mass produced from the reservoir has reached a percentage of producible fluid mass value.

In various embodiments, the controller may be configured to control the pump 208 to modify the production of fluid from the reservoir 202 based on at least one of a drainage rate, drainage speed, or drain-out time. For example, in one embodiment, the controller may control the pump 208 to modify a pressure applied to the reservoir 202 based on at least one of the drainage rate, drainage speed, or drain-out time. According to an embodiment, the controller may control the pump 208 to reduce pressure based on at least one of the drainage rate, drainage speed, or drain-out time. In other embodiments, the controller may control the pump 208 to stop the production of fluid from the reservoir based on at least one of the drainage rate, drainage speed, or drain-out time.

Embodiments of this disclosure may model fluid as capable of escaping an ultra-tight shale reservoir with a finite speed, regardless of how small the shale pores are. The model also explains why both oil and gas can be produced efficiently from shale matrix blocks to the surrounding fractures. Embodiments represent a paradigm shift from the classical Poiseuille-Darcy theory for primary petroleum production. Various embodiments of this disclosure may be applied to petroleum engineering as well as other areas of micro- or nano-scale compressible flows.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A method for production of fluid from a reservoir, the method comprising:
   receiving, by a processor, data associated with a fluid reservoir, wherein the data comprises at least a fluid viscosity in the reservoir and a pore radius in the reservoir, and wherein the data does not include a permeability of the reservoir;

modeling, by the processor and based at least in part on the data, a fluid production model comprising a reservoir fluid drainage rate that is proportional to the fluid viscosity, a reservoir fluid drainage speed that is independent of the pore radius, and a fluid drain-out time comprising a time when a total amount of fluid mass produced from the reservoir has reached a percentage of a producible fluid mass value; and operating a pump associated with the reservoir to extract fluid from the reservoir, wherein the operation of the pump is governed by the fluid production model.

2. The method of claim 1, further comprising modifying the fluid production model based on at least one of the fluid drainage rate, the fluid drainage speed, or the fluid drain-out time.

3. The method of claim 2, wherein the modifying the fluid production model comprises modifying a pressure applied to the fluid reservoir by the pump based on at least one of the fluid drainage rate, the fluid drainage speed, or the fluid drain-out time.

4. The method of claim 3, wherein the modifying the fluid production model comprises reducing the pressure applied to the fluid reservoir by the pump based on at least one of the fluid drainage rate, the fluid drainage speed, or the fluid drain-out time.

5. The method of claim 3, wherein the step of modifying the pressure comprises stopping the production of fluid from the reservoir based on at least one of the fluid drainage rate, the fluid drainage speed, or the fluid drain-out time.

6. The method of claim 1, wherein the fluid comprises petroleum.

7. The method of claim 1, wherein the fluid comprises natural gas.

8. The method of claim 1, wherein the fluid production model utilizes an equation of the form:

$$\hat{m}_e(t) = M_L \frac{D_\rho}{L^2} \sum_{n=0}^{N} \exp\left[-\frac{D_\rho(2n+1)^2\pi^2 t}{8L^2}\right].$$

9. The method of claim 1, wherein the fluid production model utilizes the Navier-Stokes equations with no-slip condition.

10. The method of claim 1, wherein the fluid production model does not utilize Darcy's law or Poiseuille's law.

11. An apparatus for producing fluid from a reservoir, comprising:

a pump which pumps a first fluid into a fluid reservoir that includes a second fluid; and a controller which controls the pump in accordance with a reservoir fluid production model, wherein the reservoir fluid production model utilizes a reservoir fluid drainage rate that is proportional to a viscosity of the second fluid in the reservoir and a reservoir fluid drainage speed that is independent of a radius of a pore in the reservoir.

12. The apparatus of claim 11, wherein the reservoir fluid production model further comprises a fluid drain-out time that provides a time when a total amount of fluid mass produced from the reservoir has reached a percentage of producible fluid mass value.

13. The apparatus of claim 12, wherein the controller controls the pump to modify a production of the fluid from the reservoir based on at least one of the fluid drainage rate, the fluid drainage speed, or the fluid drain-out time.

14. The apparatus of claim 12, wherein the controller controls the pump to modify a pressure of the first fluid pumped into the reservoir based on at least one of the fluid drainage rate, the fluid drainage speed, or the fluid drain-out time.

* * * * *